US011433174B2

United States Patent
Grueebler et al.

(10) Patent No.: US 11,433,174 B2
(45) Date of Patent: Sep. 6, 2022

(54) RETRACTABLE BACKFLUSH INSTRUMENT

(71) Applicant: Alcon Inc., Fribourg (IN)

(72) Inventors: Reto Grueebler, Greifensee (CH); Thomas Linsi, Schaffhausen (CH); Philipp Schaller, Stein am Rhein (CH)

(73) Assignee: Alcon Inc., Fribourg (CH)

( * ) Notice: Subject to any disclaimer, the term of this patent is extended or adjusted under 35 U.S.C. 154(b) by 478 days.

(21) Appl. No.: 16/709,681

(22) Filed: Dec. 10, 2019

(65) Prior Publication Data

US 2020/0188561 A1    Jun. 18, 2020

Related U.S. Application Data

(60) Provisional application No. 62/778,443, filed on Dec. 12, 2018.

(51) Int. Cl.
*A61F 9/007*    (2006.01)
*A61M 1/00*    (2006.01)
*A61M 39/22*    (2006.01)

(52) U.S. Cl.
CPC ............... *A61M 1/76* (2021.05); *A61M 1/85* (2021.05); *A61M 39/225* (2013.01); *A61F 9/00736* (2013.01)

(58) Field of Classification Search
CPC ........ A61M 1/76; A61M 1/85; A61M 39/225; A61M 1/7415; A61F 9/00736
See application file for complete search history.

(56) References Cited

U.S. PATENT DOCUMENTS

| | | | |
|---|---|---|---|
| 9,730,834 B2 | 8/2017 | Charles | |
| 9,731,065 B2 | 8/2017 | Bourne | |
| 9,750,637 B2 | 9/2017 | Schaller | |
| 9,757,536 B2 | 9/2017 | Abt | |
| 9,878,075 B2 | 1/2018 | Sussman | |
| 2005/0033309 A1 | 2/2005 | Ryan | |
| 2015/0164687 A1* | 6/2015 | Kashani | A61M 5/178 604/154 |
| 2015/0173947 A1 | 6/2015 | Charles | |
| 2016/0067091 A1 | 3/2016 | Wells | |

(Continued)

FOREIGN PATENT DOCUMENTS

CN    202426711 U    9/2012

OTHER PUBLICATIONS

Alcon Global Vitreoretinal Product Catalog, 2014 (pp. 41-48).
(Continued)

*Primary Examiner* — Nathan R Price
*Assistant Examiner* — Courtney B Fredrickson

(57) ABSTRACT

Certain embodiments provide a surgical instrument comprising a hand-piece, an outer tube having a proximal end coupled to a distal end of the hand-piece, an inner tube housed within the outer tube and having a distal end coupled to a soft tip and a proximal end coupled to an actuator, and a valve housed inside the hand-piece and coupled to the proximal end of the actuator. Retraction of the actuator is configured to compress the valve and retract the soft tip into a distal end of the outer tube, such that the soft tip at least partially extends beyond the distal end of the outer tube when the valve is in an uncompressed state and at least partially retracts into the distal end of the outer tube when the valve is a compressed state.

8 Claims, 6 Drawing Sheets

(56) References Cited

U.S. PATENT DOCUMENTS

2018/0296391 A1   10/2018  Charles
2019/0374248 A1   12/2019  Grueebler
2020/0397476 A1   12/2020  Schaller
2020/0397477 A1   12/2020  Schaller

OTHER PUBLICATIONS https://www.vitreq.com/uploads/brochures/Vitreq_BVI_Brochure_Backflush_2018.pdf (accessed May 29, 2020, appears to be dated Jun. 2018 (8 pages).
MedOne Backflush Cannulas brochure, dated 2018 (1 page).
DORC: Focus on Highlights catalog, 2012, pp. 9-11, 20, 34, 35.

* cited by examiner

RETRACTABLE BACKFLUSH INSTRUMENT

PRIORITY CLAIM

This application claims the benefit of priority of U.S. Provisional Patent Application Ser. No. 62/778,443 titled "A RETRACTABLE BACKFLUSH INSTRUMENT," filed on Dec. 12, 2018, whose inventors are Reto Grueebler, Thomas Linsi and Philipp Schaller, which is hereby incorporated by reference in its entirety as though fully and completely set forth herein.

TECHNICAL FIELD

The present disclosure relates generally to a retractable backflush instrument.

BACKGROUND

A backflush instrument is generally used during surgery (e.g., ophthalmic surgery) for vacuuming or aspirating fluids (e.g., balanced salt solution (BSS), silicone oil, perfluorcarbon (PFC)) out of a body part (e.g., a patient's eye). For example, during certain ophthalmic surgeries, a backflush instrument may be used for extracting fluids, internal drainage of subretinal fluid, retinal fold manipulation, simultaneous or sequential exchanges (e.g., fluid-air, air-gas, fluid-gas, fluid-PFC, PFC-gas, etc.). Certain backflush instruments comprise a soft, distal tip to ensure that the body part, or any tissue thereof, is not damaged when the backflush instrument makes contact with the body part or the tissue. In one example, as part of a surgery, the backflush instrument is inserted into a cannula, such as a valved cannula, in order to introduce the backflush instrument into the body part. Inserting a backflush instrument with a soft tip into a cannula, however, may be challenging and may cause damage to the backflush instrument. For example, when the backflush instrument is being inserted through the valve of a valved cannula, the soft tip may bend and get stuck in the trocar cannula. In certain cases, the soft tip may even shear off the backflush instrument if the soft tip bends excessively.

BRIEF SUMMARY

The present disclosure relates generally to a retractable backflush instrument.

Certain embodiments described herein provide a surgical instrument comprising a hand-piece, an outer tube having a proximal end coupled to a distal end of the hand-piece, an inner tube housed within the outer tube and having a distal end coupled to a soft tip and a proximal end coupled to an actuator, and a valve housed inside the hand-piece and coupled to the proximal end of the actuator. Retraction of the actuator is configured to compress the valve and retract the soft tip into a distal end of the outer tube, such that the soft tip at least partially extends beyond the distal end of the outer tube when the valve is in an uncompressed state and at least partially retracts into the distal end of the outer tube when the valve is a compressed state.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Aspects of the present disclosure provide a retractable backflush instrument.

As described above, inserting a backflush instrument with a soft tip into a cannula, such as a valved cannula can be challenging and may cause damage to the soft tip of the backflush instrument. Particular embodiments described in the present disclosure attempt to overcome these deficiencies by providing an actuator for retracting the soft tip prior to the instrument's insertion into a valved cannula, thereby preventing the soft tip from bending or being damaged during the insertion.

Figure 1:
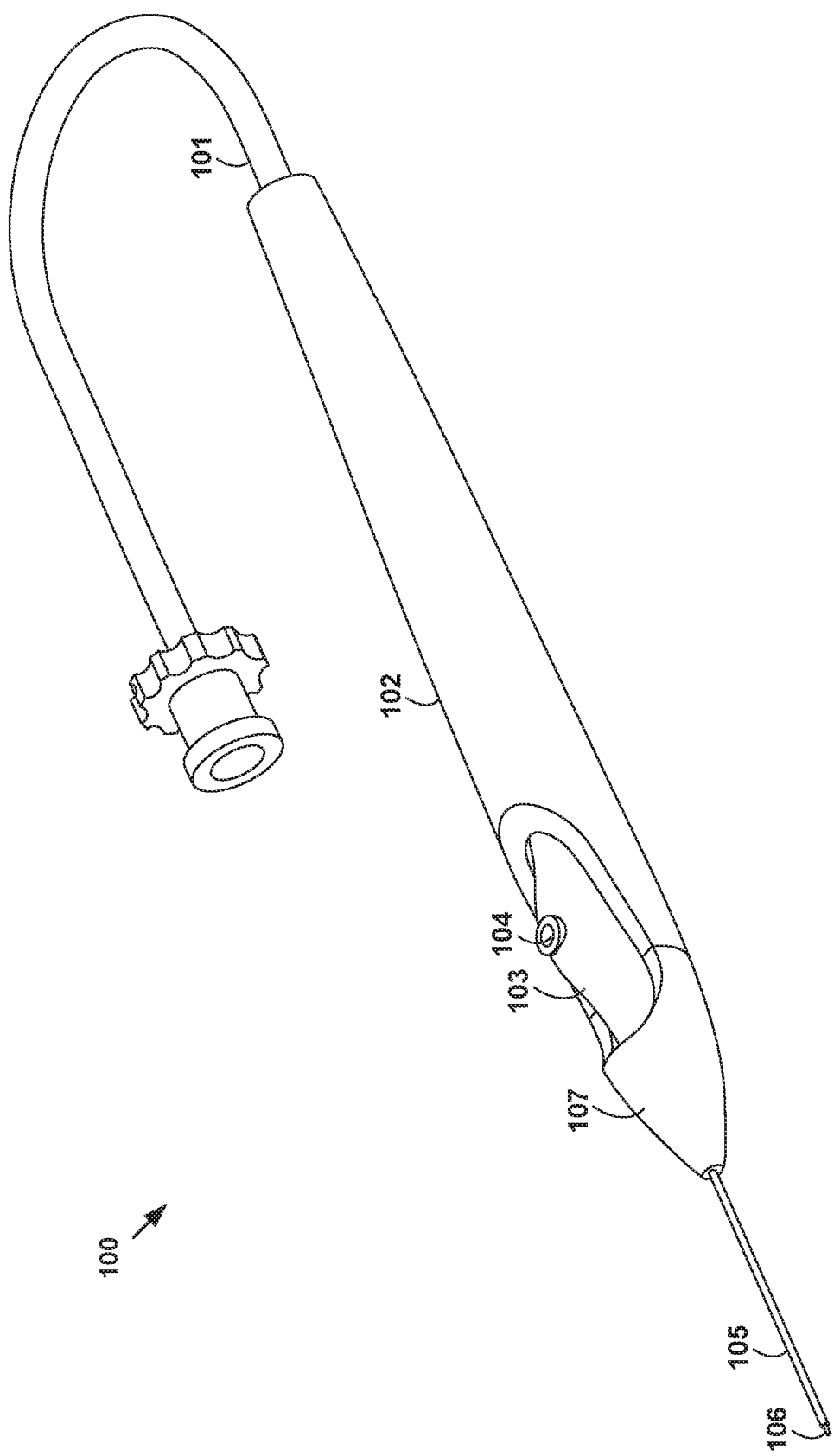
FIG. 1 illustrates a prior art example of a backflush instrument.

FIG. 1 illustrates a prior art example of a backflush instrument 100 comprising connector 101, hand-piece 102, outer tube 105, and an inner tube (e.g., inner tube 312 shown in FIG. 3) having attached a soft tip 106 that extends beyond the distal end of outer tube 105. The inner tube is a cylindrical, hollow tube that is surrounded by an outer tube 105, which is coupled to a cap 107 of hand-piece 102. The proximal end of the inner tube is coupled to valve 103, which is hose-shaped and directly or indirectly (e.g., through some other elements within hand-piece 102) coupled to connector 101. As a result, valve 103 provides a fluidic connection between the inner tube and connector 101. Valve 103 also comprises a hole 104, whose functionality varies depending on the mode in which backflush instrument 100 is operating. For example, backflush instrument 100 may be used in an active aspiration mode or a passive aspiration mode, as described below.

It should be noted that although various components are described herein with a certain shape (such as hose-shaped or cylindrical), the components may also take other similar, appropriate shapes as would be understood by one of ordinary skill in the art.

Connector 101 connects hand-piece 102 to a surgical console (not shown) with an aspiration and/or irrigation mechanism. In an example, a user, such as a surgeon, uses hand-piece 102 to guide the tip of backflush instrument 100, including outer tube 105 and soft tip 106, at least partially through a cannula and into a body part. Once inside the body part, backflush instrument 100 engages in certain operations, such as vacuuming or aspirating material (e.g., BSS, oil, or other fluids, etc.) out of the body part. During such operations, fluid flows through connector 101, valve 103, and the inner tube.

As described above, in particular embodiments, backflush instrument 100 may have two modes of operation: an active aspiration mode and a passive aspiration mode. In the active aspiration mode, backflush instrument 100 may be connected, through connector 101, to a surgical console that may actively aspirate fluids. In the active aspiration mode, the surgeon covers hole 104 (e.g., with a finger) to prevent air from being aspirated through hole 104.

In the passive aspiration mode, backflush instrument 100 is used without being connected to any surgical console through connector 101. In such an embodiment, because pressure within a body part (e.g., a patient's eye) is higher than the atmospheric pressure, when a surgeon inserts backflush instrument 100 into the body part, fluids may flow from the body part into backflush instrument 100 and exit through hole 104. In other words, in the passive aspiration mode, hole 104 may be used as a fluid outlet.

The inner tube and outer tube 105 are typically made of rigid material, such as a metal (e.g., stainless steel). Soft tip 106 is typically made of soft and flexible material (e.g., silicone, rubber, polyurethane (PUR)) as to not damage the body part with which backflush instrument 100 comes in contact. As described above, soft tip 106 is used to ensure that the body part, into which the tip of backflush instrument 100 is inserted, is not damaged. However, it may be cumbersome or impossible for a surgeon to insert backflush instrument 100 with soft tip 106 through a valved cannula. This is because when the tip of backflush instrument 100 is being pushed through the valve of the valved cannula, enough opposite force may be applied by the valve to soft tip 106 so as to bend soft tip 106. In certain cases, if the surgeon forces the bent soft tip 106 through the cannula, soft tip 106 may even separate or shear off from the inner tube.

Accordingly, certain embodiments of the present disclosure provide a backflush instrument with a retractable soft tip. Using such a backflush instrument, a surgeon is able to retract the inner tube of the backflush instrument prior to pushing the backflush instrument through a valved cannula, thereby, eliminating or reducing, the likelihood of the inner tube's tip (e.g., soft tip 106) bending or shearing off when inserted through a valved cannula.

Figure 2:
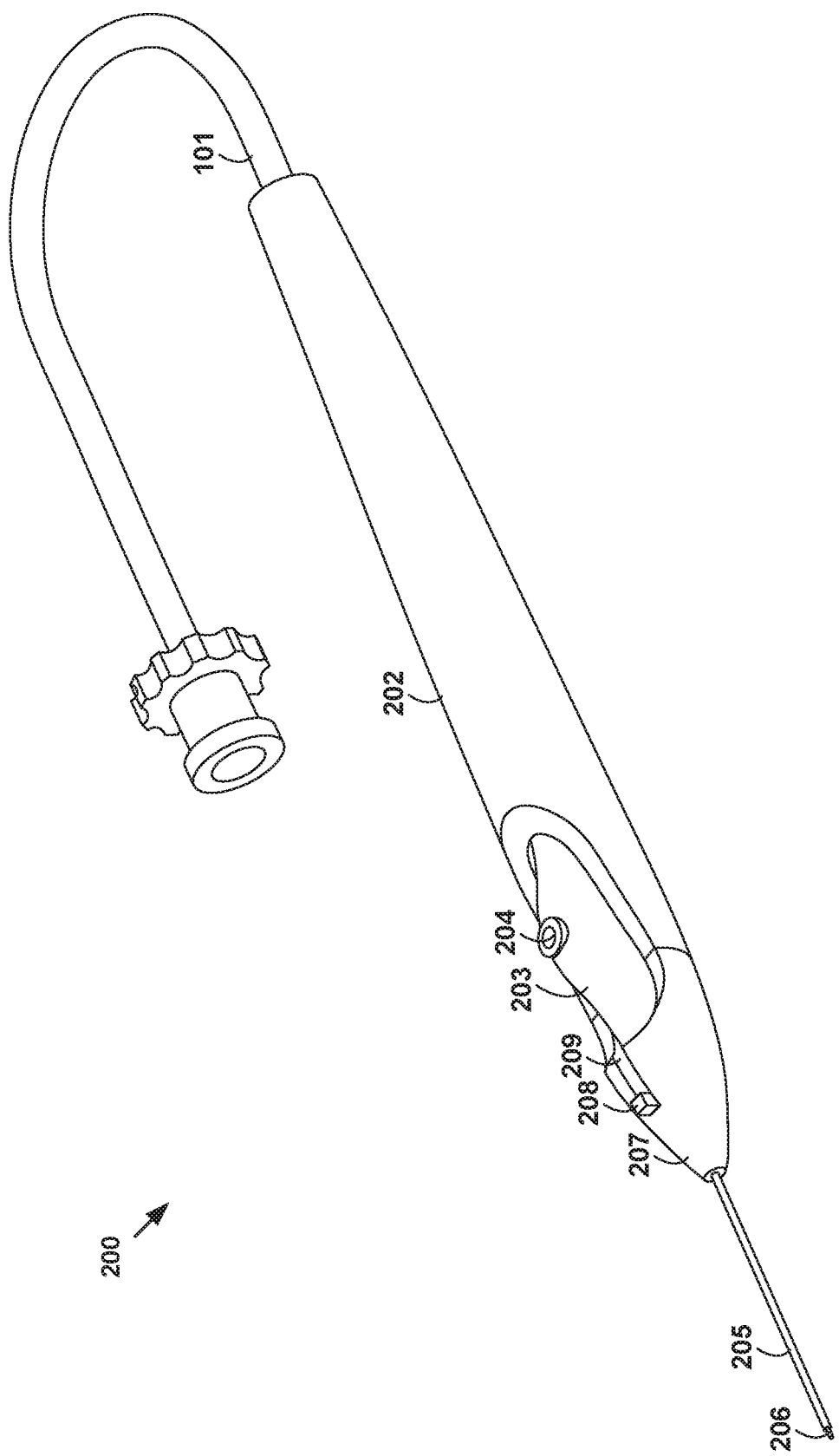
FIG. 2 illustrates an example retractable backflush instrument, according to some embodiments.

FIG. 2 illustrates an example retractable backflush instrument 200 in accordance with a particular embodiment of the present disclosure. As shown, backflush instrument 200 comprises a slider or actuator 208, which is coupled to valve 203 and configured to slide proximally through a hollow channel 209 within cap 207. More specifically, actuator 208 is configured such that it can be pulled (e.g., by a user's finger) toward the proximal end of backflush instrument 200. Actuator 208 is coupled to the proximal end of the inner tube such that pulling actuator 208 in a proximal direction retracts the inner tube. Retracting the inner tube in a proximal direction would cause soft tip 206 to no longer extend beyond the distal end of outer tube 205. Using this mechanism, a surgeon is able to retract soft tip 206, such as prior to pushing backflush instrument 200 through a valved cannula, thereby, eliminating or reducing the chance of damage to the soft tip 206. In certain embodiments, actuator 208 may be made of a plastic.

Figure 3:
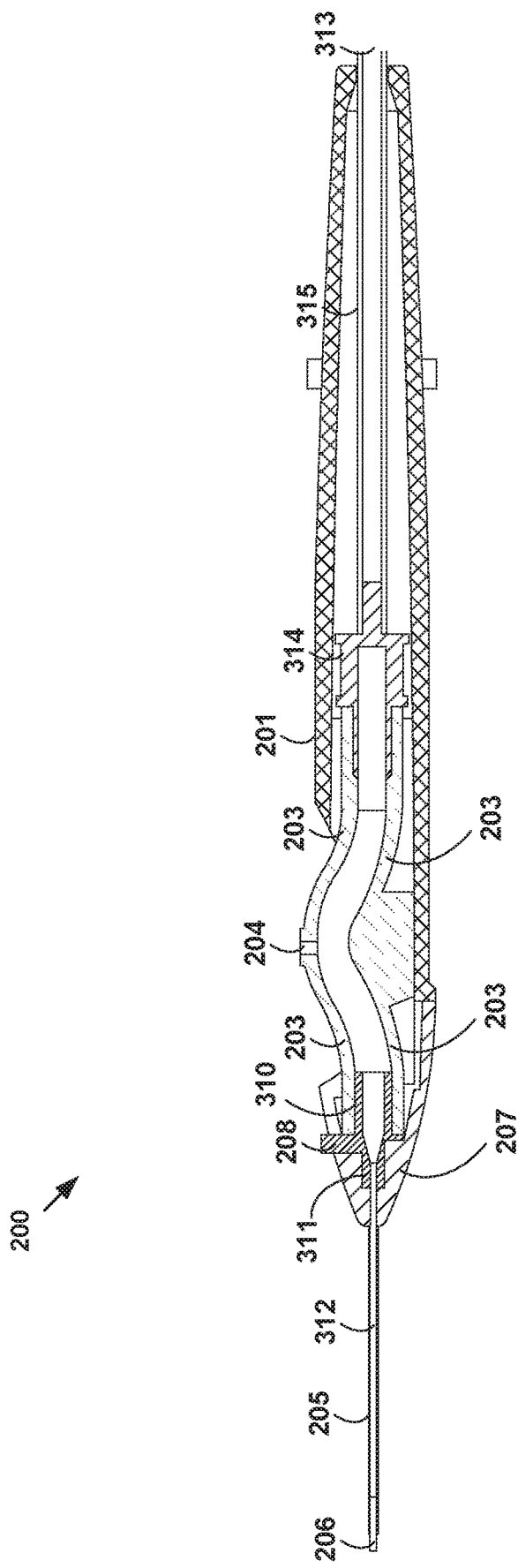
FIG. 3 illustrates a cross-sectional view of the backflush instrument of FIG. 2, according to some embodiments.

FIG. 3 illustrates an example cross-sectional view of backflush instrument 200. As shown, the distal end of actuator 208 is coupled to inner tube 312, the distal end of which is coupled to soft tip 206 that extends beyond the distal end of outer tube 205. More specifically, actuator 208 comprises a cylindrical element 311 that is configured to house the proximal end of inner tube 312. In certain embodiments, inner tube 312 and cylindrical element 311 are coupled together with the use of an adhesive. In certain embodiments, inner tube 312 and cylindrical element 311 are coupled together using insert molding techniques. In certain embodiments, the proximal end of inner tube 312 is press-fitted into cylindrical element 311. The proximal end of actuator 208 is coupled to the distal end of valve 203, which, as described above, may be tube- or hose-shaped. As shown, actuator 208 comprises a cylindrical insert 310 that is configured to be inserted into the distal end of valve 203. In certain embodiments, cylindrical insert 310 and valve 203 are coupled together with the use of an adhesive. In certain embodiments, cylindrical insert 310 is press-fitted into valve 203. Retracting actuator 208 in a proximal direction compresses valve 203, which is made of flexible and/or compressible material. For example, valve 203 may be made of silicone. A compressed valve 203 is illustrated in more detail in FIG. 4B. When a retracted actuator 208 is released, valve 203 automatically decompresses (e.g., based on spring force) and pushes actuator 208 back to its original position, thereby, causing soft tip 206 of inner tube 312 to extend beyond the distal end of the outer tube 205, as shown in FIG. 3.

As further shown in FIG. 3, at its proximal end, valve 203 is coupled to a connecting element 314 that connects the proximal end of valve 203 to a tube 315, which couples to a connector (e.g., connector 101). As shown, the proximal end of tube 315 connects with the connector at proximal end 313 of backflush instrument 200.

Although actuator 208 and valve 203 are shown as separate components, in certain embodiments, actuator 208 and valve 203 may be manufactured as one piece. For example, both actuator 208 and valve 203 may be made from the same material. In another example, actuator 208 and valve 203 may be manufactured in a two-component injection modeling process. Also, although FIG. 3 shows soft tip 206 and inner tube 312 as separate components that are attached together, in certain embodiments, inner tube 312 and soft tip 206 may be manufactured as one piece using the same material. In such embodiments, inner tube 312 is also made of flexible and soft material (e.g., silicone, PUR, etc.). Note that whether inner tube 312 and soft tip 206 are manufactured as different pieces or the same piece, they are referred to herein as being coupled to each other.

Figure 4A:
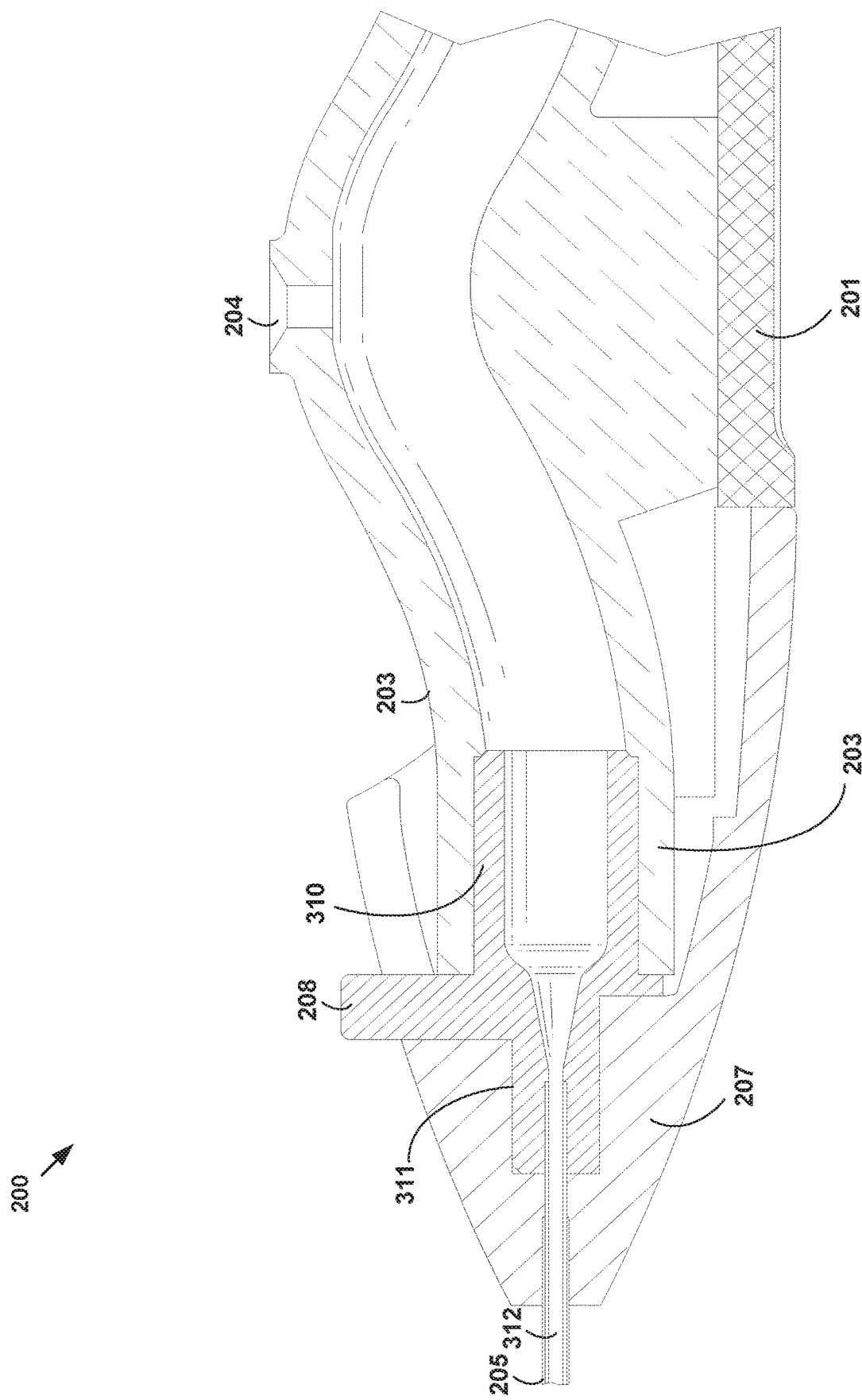
FIGS. 4A and 4B illustrate more detailed and zoomed-in views of the different states associated with the retractable actuator of the backflush instrument shown in FIGS. 2 and 3, according to some embodiments.
Figure 4B:
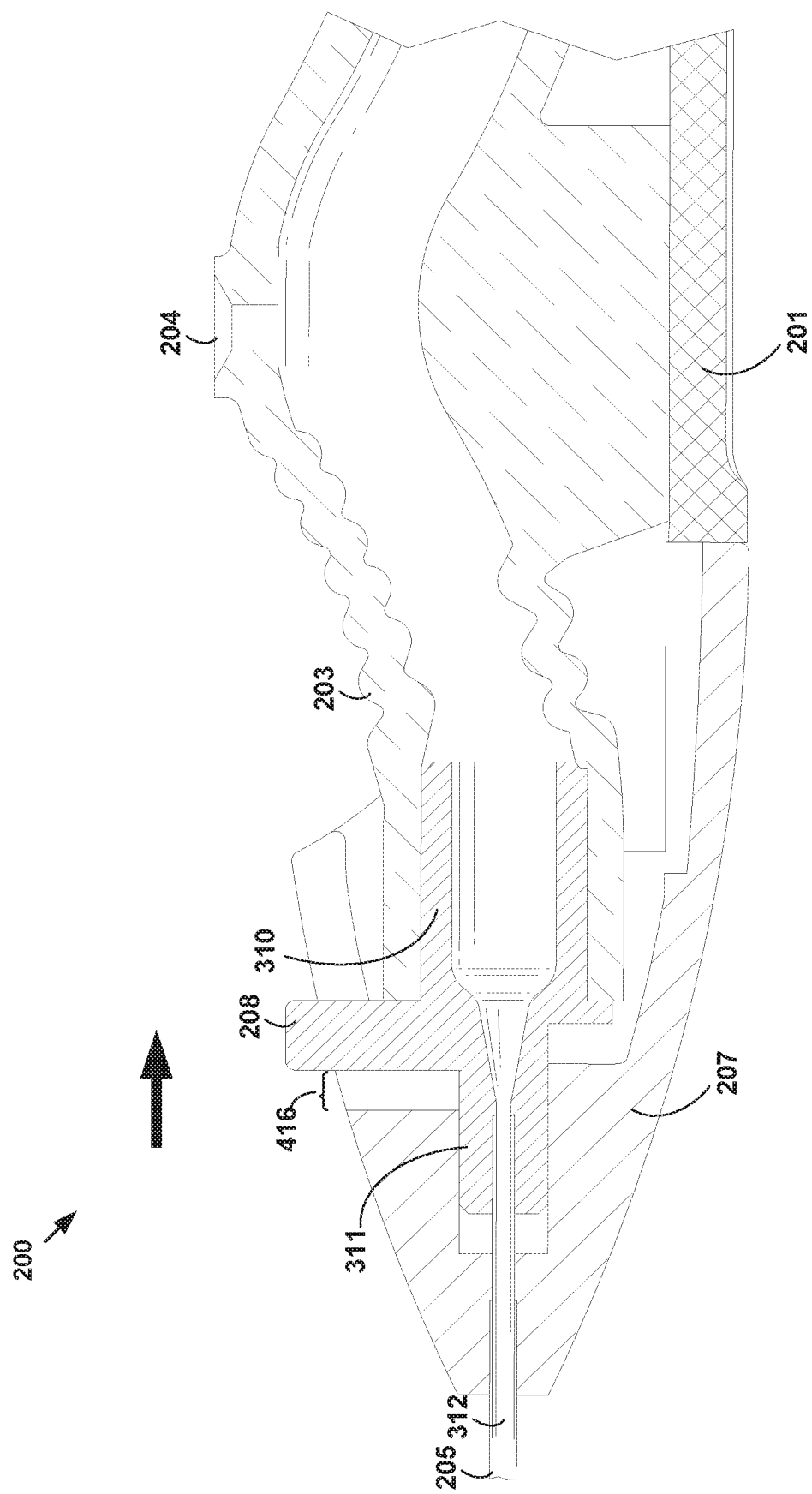

FIGS. 4A and 4B illustrate more detailed and zoomed-in views of retractable actuator 208 in different states in a particular embodiment of the present disclosure. More specifically, FIG. 4A illustrates actuator 208 at rest while FIG. 4B illustrates a retracted actuator 208. As shown in FIG. 4B, retracting actuator 208 has compressed valve 203, causing the inner and outer surfaces of valve 203 to fold in certain areas. Actuator 208 is configured to be retracted by a certain distance 416. Distance 416 may have the same length (or greater length) as soft tip 206, which is the part of inner tube 312 that extends outside of outer tube 205 when actuator 208 is at rest (e.g., when actuator 208 is not retracted). As described above, a certain amount of force (e.g., similar to a spring force) is built up into valve 203 when it is compressed such that when a retracted actuator 208 is released, the force pushes and slides actuator 208 back to its at-rest state shown in FIG. 4A.

Figure 5:
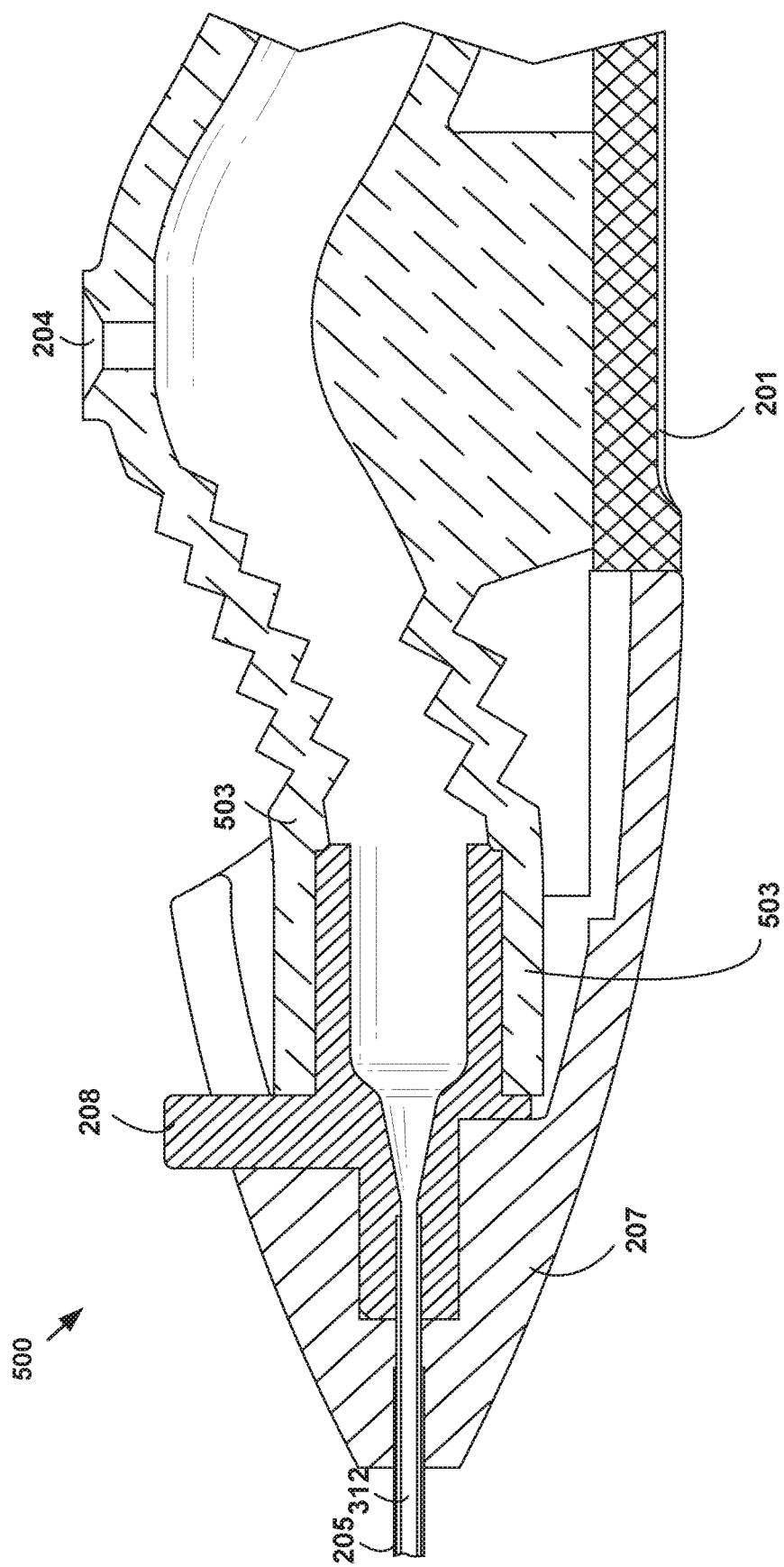
FIG. 5 illustrates an example backflush instrument with an accordion-shaped valve, according to some embodiments.

FIG. 5 illustrates a backflush instrument 500 in accordance with a particular embodiment of the present disclosure with an at-rest actuator 208 coupled to a valve 503 that is partly shaped like an accordion. In certain embodiments, because valve 503 is accordion-shaped, it may have less resistance to compression when actuator 208 is being retracted. Similarly, other shapes of valve 503 are possible within the teachings of the present disclosure which allow valve 503 to be more easily deformed and allow actuator 208 to be retracted.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. A surgical instrument, comprising:
    a hand-piece;
    an outer tube having a proximal end coupled to a distal end of the hand-piece;
    an inner tube housed within the outer tube and having a distal end coupled to a soft tip and a proximal end coupled to an actuator; and
    a valve comprising an exterior hole housed inside the hand-piece and coupled to the proximal end of the actuator;
    wherein retraction of the actuator is configured to compress the valve; and
    wherein the soft tip at least partially extends beyond a distal end of the outer tube when the valve is in an uncompressed state and at least partially retracts into the distal end of the outer tube when the valve is in a compressed state.

2. The surgical instrument of claim 1, wherein the surgical instrument comprises a backflush instrument.

3. The surgical instrument of claim 1, wherein the actuator comprises:
    a cylindrical insert configured to be inserted into a distal end of the valve; and
    a cylindrical element configured to house the proximal end of the inner tube.

4. The surgical instrument of claim 1, wherein the valve is accordion shaped.

5. The surgical instrument of claim 1, wherein the actuator comprises plastic material.

6. The surgical instrument of claim 1, wherein the hand-piece comprises a cap for housing the actuator at the distal end of the hand-piece.

7. The surgical instrument of claim 6, wherein the cap comprises a hollow channel through which the actuator is able to retract.

8. The surgical instrument of claim 7, wherein the actuator partially extends outside of the hollow channel to allow hand manipulation for retracting and releasing the actuator.

* * * * *